United States Patent [19]

Hofsess

[11] Patent Number: 4,975,053
[45] Date of Patent: Dec. 4, 1990

[54] DEVICE FOR PLACEMENT, SEATING AND CEMENTATION OF A RESTORATIVE ELEMENT ONTO A TOOTH

[75] Inventor: Paul W. Hofsess, Vernon, Conn.

[73] Assignee: John L. Voellmicke, Franklin Lakes, N.J. ; a part interest

[21] Appl. No.: 404,347

[22] Filed: Sep. 5, 1989

[51] Int. Cl.⁵ .............................................. A61C 5/12
[52] U.S. Cl. .................................... 433/25; 433/215; 433/218
[58] Field of Search ..................... 433/68, 25, 71, 167, 433/136, 40, 138, 140, 141, 163, 218, 229, 39, 1, 223, 215

[56] References Cited

U.S. PATENT DOCUMENTS

| | | | |
|---|---|---|---|
| 3,974,567 | 8/1976 | Ridgeway | 433/218 |
| 4,219,619 | 8/1980 | Zarow | 433/118 |
| 4,664,628 | 5/1987 | Totaro | 433/136 |
| 4,773,857 | 9/1988 | Herrin | 433/138 |
| 4,919,615 | 4/1990 | Croll | 433/3 |

OTHER PUBLICATIONS

Jada, vol. 117, Dec. 1988, "Improving the Cementation of Complete Cast Crowns: A Comparison of Static and Dynamic Seating Methods", pp. 845-848.
Jada, vol. 117, Oct. 1988, "Pulmonary Aspiration of a Metal Casting: Report of Case", pp. 587-588.

Primary Examiner—Cary E. Stone

[57] ABSTRACT

A device for the placement, seating and cementation of a restorative element having a top surface, onto a tooth comprises a flexible strip portion having a top surface, a bottom surface and a bite element for allowing the patient to apply dynamic biting pressure to the restorative element to position and hold the restorative element in its proper seated position on the tooth. Adhesive is provided on the bottom surface of the flexible strip portion for removably securing the strip portion to the restorative element and for positioning the bite element adjacent to the top surface of the restorative element.

20 Claims, 5 Drawing Sheets

DEVICE FOR PLACEMENT, SEATING AND CEMENTATION OF A RESTORATIVE ELEMENT ONTO A TOOTH

BACKGROUND OF THE INVENTION

1. Field of the Invention

The present invention relates to restorative elements such as crowns which are attached to teeth and more particularly concerns a device for the placement, seating and cementation of a restorative element such as a crown onto a tooth.

2. Description of Related Information

Generally speaking, it is common dental practice to partially remove an exposed portion of a tooth such as molar or bicuspid. That portion of the tooth remaining is permanently engaged by a restorative element, such as a crown, which has substantially the same external configuration as the original tooth. The restorative element or crown is bonded to the remaining portion of the tooth using cement.

When placing a restorative element, such as a crown, onto a tooth, such as a molar, the dentist must assure that the crown is properly placed and seated and restrained in a seated position while the cement between the crown and the molar solidifies.

It is believed that dynamic loading is superior to static loading for seating and holding the crown during the cementation process. The dynamic loading works the crown into its proper seated position while expelling air and excess cement. Rosenstiel and Gegauff in their Journal of the American Dental Association article of Dec., 1988 demonstrate the superiority of dynamic seating methods over static seating methods for the cementation of complete cast crowns. Dynamic seating force can be applied with the use of an orange wood stick where the dentist and the patient work together to provide dynamic loading on the newly placed crown. In this procedure the dentist controls the orange wood stick while the patent provides a variety of biting forces on the stick, against the crown, as instructed by the dentist.

Zarro in U.S. Pat. No. 4,219,619 teaches a form of dynamic loading using a vibrator utilizing a disposable bite probe.

During the placement and cementation process which is demanding of the dentist's attention he or she must also be ever alert to the safety of the patient. A loose crown could accidentally be swallowed by the patient or, more seriously, be aspirated by the patient. Aspiration of a crown leads to serious medical complications with respect to the after effects of the aspiration and removal of the crown. Many cases of crown operation have been documented with some unfortunately leading to the death of the patient. Seals, Adry and Kellar in their Journal of the American Dental Association article of Oct., 1988 discuss pulmonary aspiration of a metal casting and the danger of ingesting or aspirating a foreign body by a patient during dental treatment. The article discusses the prevention and management of this event.

In addition, devices have been developed and are readily commercially available to help prevent ingestion and aspiration of foreign bodies during dental treatment. A rubber dam or sheet of plastic material is commonly used to cover the throat and airways in the rear of the mouth during dental procedures which have a high potential for generating debris. U.S. Pat. No. 4,664,628 to Totaro teaches such a device. These devices are very difficult to use and compromise the dentist's and the patient's ability to optimize the cementation process by occupying the limited space of the oral cavity, distracting the patient, severely limiting the patient's ability to provide biting forces, and limiting the space available for activities associated with the procedure.

The prior art has provided teachings and devices to provide for dynamic seating forces during the placement, seating and cementation of crowns and has also provided teachings and devices to help prevent the ingestion and aspiration of a foreign body during dental treatment. However, there is still a need for a simple, straight forward, reliable, easily fabricated device for the placement, seating and cementation of a restorative element onto a tooth which provides for the application of dynamic seating forces to the restorative element while helping to prevent aspiration or ingestion of the restorative element during the procedure.

SUMMARY OF THE INVENTION

A device of the present invention for the placement, seating and cementation of a restorative element having a top surface, onto a tooth comprises a flexible strip portion having a top surface, a bottom surface, and bite means for allowing the patient to apply dynamic biting pressure to the restorative element to position and hold the restorative element in its proper seated position on the tooth. Adhesive means is provided on the bottom surface of the flexible strip for removably securing the strip to the restorative element and for positioning the bite means adjacent to the top surface of the restorative element.

In a preferred embodiment of the present invention, a device for placement seating and cementation of a crown onto a tooth, said crown having a top surface and a side wall defining an interior cavity for receiving said tooth, comprises a flexible strip portion having opposed first and second ends and a central portion therebetween. The strip includes a top surface and a bottom surface. Bite means is provided at the central portion for allowing the patient to apply dynamic biting pressure to the crown to work the crown into its proper seated position on the tooth. Adhesive means is provided on the bottom surface for removably securing the strip to the crown and for positioning the bite means adjacent to the top surface of the crown. The adhesive means is covered with removable release sheet for protecting the adhesive means before the time of use. An elongate safety string means may also be connectably associated with the strip for preventing the device from being aspirated or ingested by the patient. The safety string means is long enough to protrude from the patient's mouth while adhesive means is attached to the restorative element and the restorative element is on the tooth during the cementation procedure.

DETAILED DESCRIPTION

Figure 1:
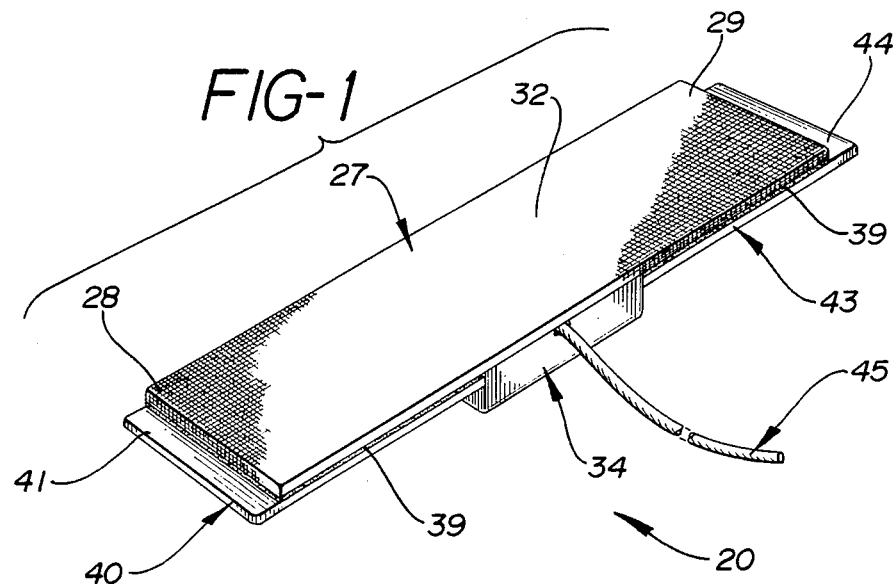
FIG. 1 is a perspective view of the device for placement, seating and cementation of a restorative element of the present invention.
Figure 2:
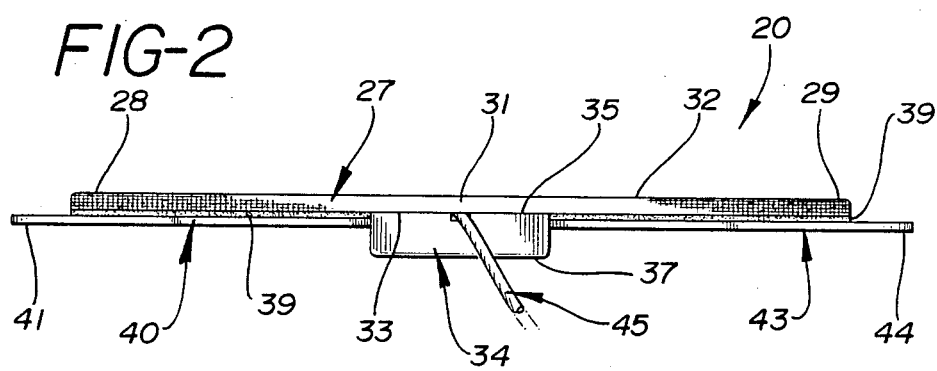
FIG. 2 is a front elevational view of the device of FIG. 1.
Figure 3:
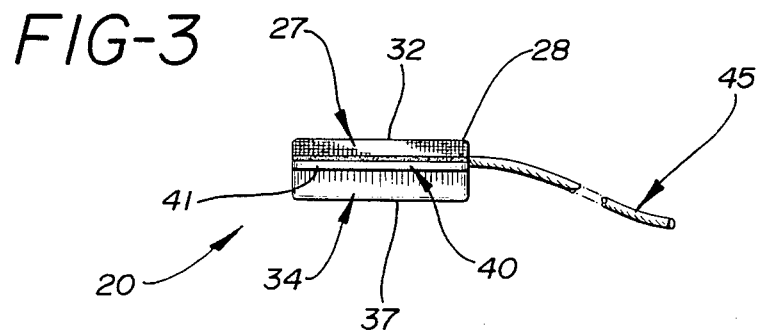
FIG. 3 is a side elevational view of the device of FIG. 2.

While this invention is satisfied by embodiments in many different forms, there are shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1-6, a device 20 for placement, seating and cementation of a restorative element such as a crown onto a tooth wherein a crown 21 includes a top surface 22 and a side wall 23 defining an interior cavity 25 for receiving the tooth includes a flexible strip portion 27. The flexible strip portion includes a first end 28 and a second end 29 opposed from each other having a central portion 31 therebetween. The strip portion includes top surface 32 and bottom surface 33.

For the purposes of the description of the present invention the term "top" is meant to refer to that side of the strip or device which is furthest away from the crown or restorative element while the term "bottom" is meant to refer to the side of the strip or the device which is closest to the crown or restorative element. Also the term top surface of the crown or restorative element is meant to refer to an outside surface on the crown or restorative element used for biting and closest to bottom side of the strip.

Figure 6:
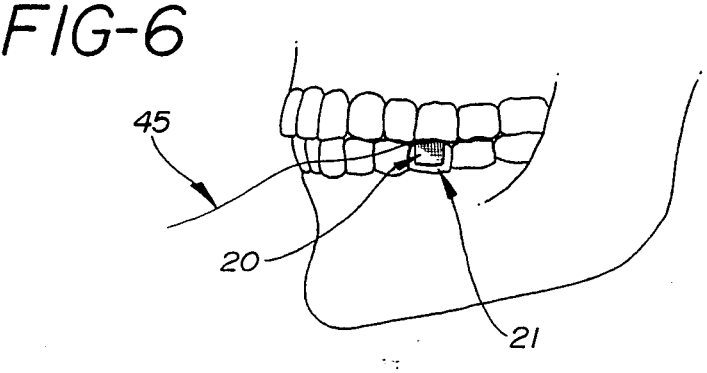
FIG. 6 is illustrative of a patient using the device of the present invention to place dynamic loading on a crown to provide for proper seating and cementation.

Bite means in the form of a bite block 34 is provided at central portion 31 for allowing the patient to apply dynamic biting pressure to the crown (as best illustrated in FIG. 6) to work the crown into its proper seated position on the tooth as will be explained in more detail hereinafter. In this preferred embodiment the bite block is rectangularly shaped when viewed from the front and includes top surface 35 which is parallel to a bottom surface 37. The bite block is preferably made of a resilient material such as rubber which should be hard enough to allow the patient to transmit dynamic biting pressure to the crown for proper seating yet have some resilience to distribute the forces.

Figure 4:
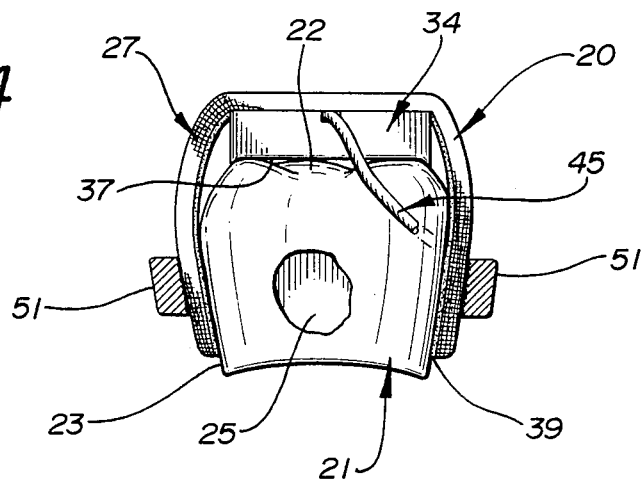
FIG. 4 is a front elevational view of the device of FIG. 1 attached to a crown with the crown being held by forceps.

An adhesive 39 is provided on bottom surface 33 of strip portion 27 for removably securing the strip portion to the crown and for positioning bite block 34 adjacent to top surface 22 of the crown as best illustrated in FIG. 4. A removable release sheet 40 covers adhesive 39 at first end 28 of the strip portion and protects the adhesive before the time of use. Release sheet 40 also includes overhanging gripping tab 41 to facilitate the easy removal of release sheet 40 from adhesive 39 by providing a portion of the release sheet which is easily grasped for removal by the user. In addition, a release sheet 43 covers adhesive 39 at second end 29 of the strip. Release sheet 43 also includes an overhanging gripping tab 44 to facilitate easy removal of release sheet 43.

To help prevent accidental ingestion or aspiration of the crown by the patient, this preferred embodiment includes an elongate safety string 45 connectively associated with the strip portion. Safety string 45 is long enough to protrude from the patient's mouth (as best illustrated in FIG. 6) while adhesive is attached to the crown and the crown is positioned in the patient's mouth on the patient's tooth. The safety string is preferably within the range of 5 cm to 30 cm long. In this preferred embodiment the safety string is made of relatively flat plastic film having a rectangular cross-section. Strong thin films are well known in the art and are used to make numerous tape and similar products.

In this preferred embodiment the flat safety string is conveniently attached to the device by trapping its distal end between strip portion 27 and bite block 34 at the time of assembly. It may be convenient to use adhesive 39 to attach bite block 34 to flexible strip portion 27 and to secure safety string 45 therebetween. It will be apparent to one skilled in the art that there are numerous ways of attaching a bite block to a flexible strip including the use of mechanical means, adhesive, ultrasonic welding, heat sealing, sewing or other suitable means depending on the materials chosen for the bite block and the flexible strip portion, and that the structure illustrated in the preferred embodiment using adhesive is exemplary of these many possibilities all of which are within the purview of the instant invention. It will also be apparent to one skilled in the art that there are numerous ways to connectively associate an elongate safety string with the flexible strip portion and/or the bite block including passing the string through an aperture in one or both of these elements and tying the string into a knot, adhesives, mechanical means, ultrasonic welding, heat sealing or other suitable means depending on the materials chosen and that the trapping of the distal end of the string between the bite block and the strip means is exemplary of these many possibilities which are all within the purview of the instant invention.

In this preferred embodiment the strip portion is a rectangularly shaped sheet approximately 2.5 cm long and 1 cm wide when viewed from the top surface. However, the strip portion need not be rectangularly shaped or flat, and the overall dimensions of the strip portion will depend on the size of the restorative element being used and the size and position of the bite block. For example, a large bite block attached to the bottom surface of the strip portion will require a longer strip portion than if the bite block is attached to the top surface of the strip portion. A strip portion having a surface area of between about 0.3 cm$^2$ and 6.0 cm$^2$ should be satisfactory for most applications.

In use, the dentist prepares a tooth 50 for receiving a crown and participates in the design and formation of crown 21 to properly fit the patient using well-known devices and techniques. When the crown is ready for permanent attachment to the tooth the dentist, using the preferred embodiment of the instant invention, removes release sheets 40 and 43 from the strip portion by grasping gripping tabs 41 and 44 respectively and pulling the release sheets from the adhesive on the strip portion.

Device 20 is now placed on the crown so that bite block 34 is adjacent to top surface 22 of the crown and the first and second ends of the strip are adjacent to the side wall of the crown with safety string 45 projecting outwardly from the side of the device which is aligned with the front of the cap. Digital pressure should now be applied to attach the first and second ends of the strip portion firmly to side wall 23 of the crown. The appropriate cement should then be placed in interior cavity 25 of the crown and the entire assembly firmly grasped with forceps 51 for placement of the crown on the tooth.

It should be noted that the strip portion helps to protect the crown from the hard surface of the forceps while still allowing a firm control and grip on the crown. The strip material may be especially chosen to provide for protection of the crown under the aggressive grip of the forceps. Crown protection is an important feature of the instant invention.

Figure 5:
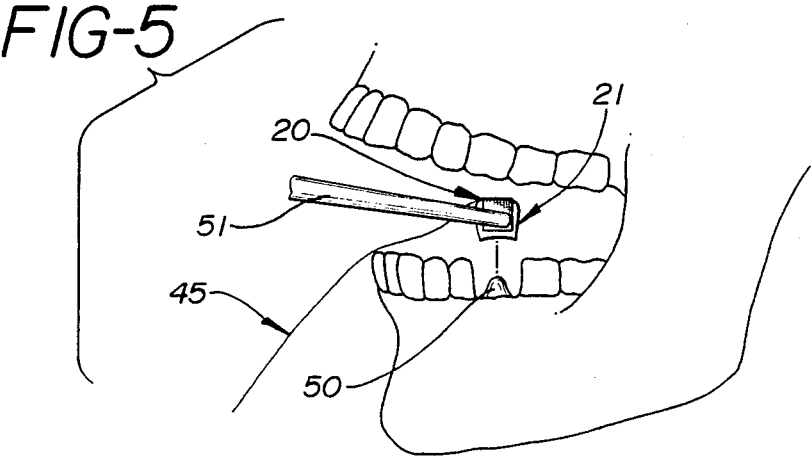
FIG. 5 is a side elevational view of the crown device and forceps assembly of FIG. 4 and a patient's jaws, illustrating the crown being placed upon a tooth.

The crown is now inserted into the mouth, as illustrated in FIG. 5, using the forceps to position it upon tooth 50. At this time the dentist has excellent control over the position of the crown through using the forceps and he is free to move the crown within the oral cavity without interference from a rubber dam or other throat blocking device because safety string 45 is provided to protect the patient from inadvertent aspirating or ingesting the crown should it become loose during the cementation process.

The crown is now placed on the tooth while the dentist grasps the safety string and removes the forceps and instructs the patient to bite down to hold the crown on the tooth. At this time the patient will provide dynamic biting forces to the crown through the bite block by forcing upper teeth 52 against the bite block in a plurality of various biting motions, as instructed by the dentist, to properly seat the crown onto the tooth during the cementation process. The patient, using biting force, holds the crown in place until the cement cures. At this time the crown is properly placed and permanently attached to the tooth. The dentist may then remove device 20 by peeling the strip portion off the crown and removing the device from the patient's mouth while holding the safety string. It can be seen that the device for placement, seating and cementation of a crown to a tooth of the instant invention has substantial structural and functional advantages over the devices and teachings of the prior art including proper and easy crown placement and seating using dynamic forces and protection of the patient without undue apparatus which could interfere with the procedure.

Figure 7:
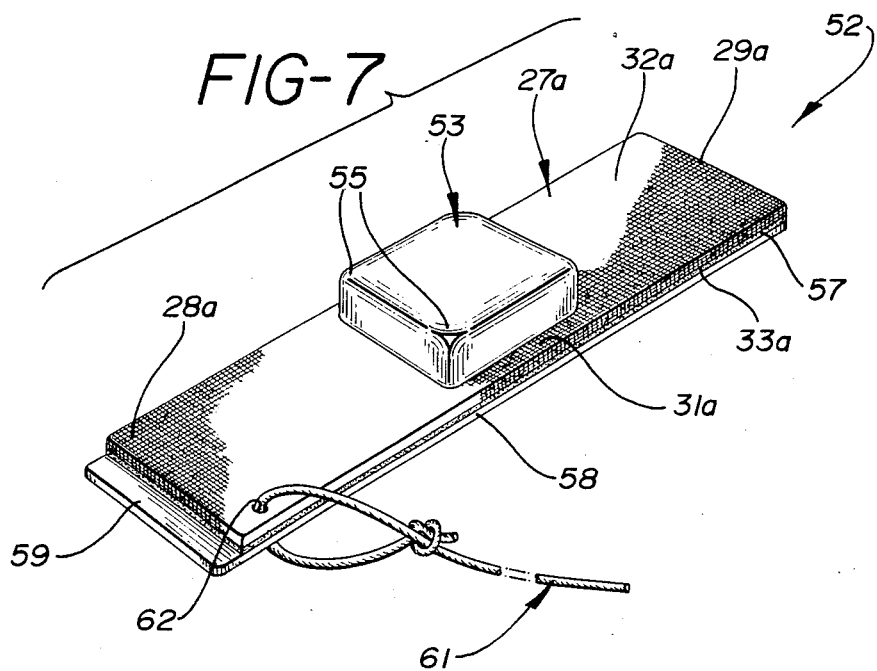
FIG. 7 is a perspective view of an alternative embodiment of the device for placement, seating and cementation of a restorative element of the present invention.

Referring now to FIG. 7, an alternative embodiment of the device for the placement, seating and cementation of a restorative element onto a tooth is illustrated. In this alternative embodiment the structure of the device is substantially similar to the device of FIGS. 1–6. Accordingly, substantially similar components that perform substantially similar functions will be numbered identically to those components of the embodiment of FIGS. 1–6 except a suffix "a" will be used to identify those components shown in FIG. 7. In this alternative embodiment, a device 52 for the placement, seating and cementation of a restorative element onto a tooth includes a flexible strip portion 27a having a first end 28a and a second end 29a and a central portion 31a therebetween. Strip 27a includes a top surface 32a and a bottom surface 33a.

A bite block 53 having rounded corners 55 is attached to top surface 32a for allowing the patient to apply dynamic biting pressure to a restorative element to hold the restorative element in its proper seated position on the tooth. Adhesive 57 is applied to bottom surface 33a for removably securing the strip to the restorative element and for positioning the bite block adjacent to the top surface of the restorative element. Adhesive 57 is covered by removable release sheet 58 having gripping tab 59 to facilitate its removal at the time of use. It is within the purview of this invention to provide a strip portion having a bottom surface which is entirely covered with adhesive or partially covered with adhesive depending on the application. Safety string 61 is connected to the strip portion for preventing the device from being aspirated or ingested by the patient. The safety string should be long enough to protrude from the patient's mouth while the adhesive is attached to the restorative element in the patient's mouth. The safety string 61 of this embodiment has a string like structure such as thread or dental floss and is attached to strip portion 27a through an aperture 62 which may be punched through the strip portion, the adhesive and the backing sheet. The safety string 61 is passed through the aperture and tied into a knot to secure it. At the time of use the string will cause the release sheet to tear around the aperture as it is being removed from the adhesive.

This embodiment serves to illustrate the many different means for attaching the safety string to the device and the various placements of the bite block including on the top surface of the strip portion or the bottom surface of the strip portion, or integrally fabricated as part of the strip portion. Also the bite block does not have to be firmly attached to the strip and may be contained by other retaining means which serve to hold it in relative position during use. It will be apparent that the block may have freedom of motion with respect to the strip so long as the bite block is properly aligned at the time of use. Also, the block should be safely attached to or connectively associated with the strip to avoid ingestion of the block by the patient during the procedure.

Figure 8:
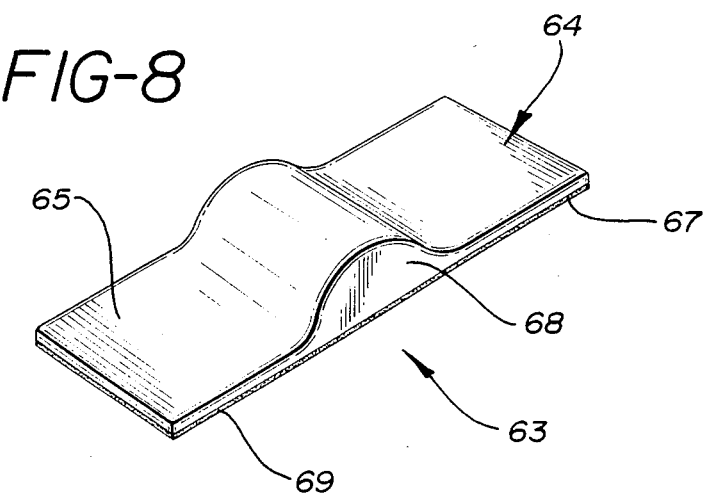
FIG. 8 is a perspective view of still another alternative embodiment of the device for placement, seating and cementation of a restorative element of the present invention.

Referring now to FIG. 8, another alternative embodiment of the instant invention is illustrated. In this alternative embodiment, a device 63 for the placement, seating and cementation of a restorative element having a top surface, onto a tooth includes a flexible strip portion 64 having a top surface 65 and a bottom surface 67 and an integrally formed bite block 68 for allowing the patient to apply dynamic biting pressure to the restorative element to hold the restorative element in its proper seated position on the tooth. Adhesive 69 is provided on bottom surface 67 for removably securing the strip portion to the restorative element and for positioning the bite block adjacent to the top surface of the restorative element during use. In this embodiment the flexible strip portion is formed of an elongate elastomeric flexible material from which is cut into strips which are perpendicular to the major axis of the form so that the bite block and the flexible strip portion are integrally formed of one piece. The adhesive may be added before cutting the individual strips, along with the backing sheet if a backing sheet is used, to simplify manufacturing procedures.

The bite block of the present invention may be formed of a wide variety of materials as an individual element or integrally with the flexible strip portion. Desirable materials for the bite block include natural rubber, synthetic rubber, thermoplastic elastomer, thermoplastic and wood.

A wide variety of flexible materials and fabrics are suitable for the flexible strip portion with non woven fabric, woven fabric, thermoplastic, natural rubber, synthetic rubber, natural rubber latex, synthetic rubber latex and thermoplastic elastomers being desirable. Cotton flannel material is very desirable since it can provide a thick rough surface for grasping with a forceps while protecting the crown and being resilient to tearing woven and non-woven cotton materials are also desirable.

A wide variety of materials are suitable for adhesive with water-based acrylic adhesives being desirable. Again, the choice of adhesive will depend on the choice of strip portion material. A wide variety of materials are suitable for a release sheet wherein the choice is primarily determined by the choice of adhesive. Silicone impregnated paper is a desirable release sheet used in many applications.

It may sometimes be desirable for the elements of the device of the present invention to be sterile when used. When sterility is a requirement, materials should also be selected for their compatibility with the sterilization process being used.

Thus, it can be seen that the present invention provides a simple, straight-forward, reliable, easily fabricated device for placement, seating and cementation of the restorative element, such as a crown, onto a tooth which provides for the application of dynamic seating forces to the restorative element while helping to prevent aspiration or ingestion of the restorative element during the procedure. The strip portion of the device of the present invention also provides a convenient surface for grasping the restorative element with a forceps for controlling the position of the restorative element while helping to protect it from surface damage caused by the hand forceps.

What is claimed is:

1. A device for placement, seating and cementation of a restorative element having a top surface and a side surface, onto a tooth comprising:
   a flexible strip portion having opposed first and second ends and a central portion therebetween, said strip portion having a top surface and a bottom surface;
   bite means at said central portion for allowing the patient to apply dynamic biting pressure to said restorative element to position and hold said restorative element in its proper seated position on the tooth; and
   adhesive means on said bottom surface for removably securing said strip to said restorative element and for positioning said bit means adjacent to said top surface of said restorative element and said first and second ends adjacent to said side surface.

2. The device for placement, seating and cementation of a restorative element of claim 1 wherein said adhesive means is covered with a removable release sheet for protecting said adhesive means before time of use.

3. The device for placement, seating and cementation of a restorative element of claim 1 wherein said adhesive means is on a portion of said first end and a portion of said second end.

4. The device for placement, seating and cementation of a restorative element of claim wherein said bite means is integrally formed with said strip.

5. The device for placement, seating and cementation of a restorative element of claim 1 wherein said bite means is attached to said strip.

6. The device for placement, seating and cementation of a restorative element of claim 5 wherein said bite means is attached to said top surface of said strip.

7. The device for placement, seating and cementation of a restorative element of claim 1 wherein said bite means has a thickness within the range of about 0.5mm to 6 mm.

8. The device for placement, seating and cementation of a restorative element of claim 1 further including an elongate safety string means connectively associated with said strip for helping to prevent said device from being aspirated or ingested by the patient, and safety string means being long enough to protrude from the patient's mouth while said adhesive means is attached to said restorative element and said restorative element is on the tooth.

9. The device for placement, seating and cementation of a restorative element of claim 8 wherein said safety string means is within the range of about 5 cm to 30 cm long.

10. The device for placement, seating and cementation of a restorative element of claim 8 wherein said safety string means is made of thermoplastic sheet material.

11. The device for placement, seating and cementation of a restorative element of claim 1 wherein said strip portion is made from material selected from the group consisting of non-woven fabric, woven fabric, thermoplastic, natural rubber, synthetic rubber, thermoplastic elastomer, natural rubber latex and synthetic rubber latex.

12. The device for placement, seating and cementation of a restorative element of claim 1 wherein said strip portion is made of material selected from the group consisting of woven cotton fabric and non-woven cotton fabric.

13. The device for placement, seating and cementation of a restorative element of claim 1 wherein said bite means is made of material selected from the group consisting of natural rubber, synthetic rubber, thermoplastic elastomer, thermoplastic and wood.

14. The device for placement, seating and cementation of a restorative element of claim 1 wherein said strip portion has an area of between 0.3 cm² and 6.0 cm².

15. A device for placement, seating and cementation of a crown onto a tooth, said crown having a top surface and a side wall defining an interior cavity for receiving said tooth, comprising:
   a flexible strip portion having opposed first and second ends and a central portion therebetween, said strip portion having a top surface and a bottom surface;
   bite means at said central portion for allowing the patient to apply dynamic biting pressure to said crown to work said crown into its proper seated position on the tooth;
   adhesive means on said bottom surface for removably securing said strip portion to said crown and for positioning said bite means adjacent to the top surface of said crown and said first and second ends adjacent to said side wall of said crown; and
   said adhesive means being covered with a removably release sheet for protecting said adhesive means before time of use.

16. The device for placement, seating and cementation of a crown of claim 15 wherein said adhesive means is on a portion of said first end and a portion of said second end.

17. The device for placement, seating and cementation of a crown of claim 15 further including an elongate safety string means connectively associated with said strip for helping to prevent said device from being aspirated or ingested by the patient, said safety string means being long enough to protrude from the patient s mouth while said adhesive means is attached to said crown and said crown is on the tooth.

18. The device for placement, seating and cementation of a crown of claim 15 wherein said strip portion is made from material selected from the group consisting of non woven fabric, woven fabric, thermoplastic, natural rubber, synthetic rubber, thermoplastic elasomter, natural rubber latex and synthetic rubber latex.

19. The device for placement, seating and cementation of a crown of claim 15 wherein said bite means is made of material selected from the group consisting of natural rubber, synthetic rubber, thermoplastic elastomer, thermoplastic and wood.

20. A method for placement, seating and cementation of a crown onto a tooth, said crown having a top surface and a side wall defining an interior cavity for receiving said tooth, using a device including:

a flexible strip portion having opposed first and second ends and a central portion therebetween, said strip portion having a top surface and a bottom surface;

bite means at said central portion for allowing the patient to apply dynamic biting pressure to said crown;

adhesive means on said bottom surface for removably securing said strip to said crown;

said method comprising the step of:
 (a) attaching said device to said crown so that said bite means is adjacent to said top surface of said crown with said adhesive means contacting crown and said first and second ends adjacent to said side wall of said crown;
 (b) placing a quantity of cement in said interior cavity of said crown;
 (c) grasping the assembly of said crown and said device with a forceps so that the forceps contacts said first and second ends of said flexible strip portion;
 (d) using said forceps to place said crown on said tooth;
 (e) releasing said forceps from said assembly while causing the patient to apply biting forces on the crown through said bite means; and
 (f) removing said device from said crown after said crown is attached to said tooth.

* * * * *